(12) United States Patent
Preinitz

(10) Patent No.: US 9,101,340 B2
(45) Date of Patent: Aug. 11, 2015

(54) INSERTION TOOL FOR A CLOSURE DEVICE

(75) Inventor: Fredrik Preinitz, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 2076 days.

(21) Appl. No.: 12/078,465

(22) Filed: Mar. 31, 2008

(65) Prior Publication Data

US 2009/0248064 A1    Oct. 1, 2009

(51) Int. Cl.
*A61F 2/06*    (2013.01)
*A61B 17/00*    (2006.01)

(52) U.S. Cl.
CPC ... *A61B 17/0057* (2013.01); *A61B 2017/00398* (2013.01); *A61B 2017/00575* (2013.01); *A61B 2017/00619* (2013.01); *A61B 2017/00623* (2013.01)

(58) Field of Classification Search
CPC .................. A61B 17/0057; A61B 2017/00398; A61B 2017/00623; A61B 2017/00619; A61B 2017/00575
USPC ......... 606/213, 214, 215, 216, 217, 218, 219, 606/220, 221
See application file for complete search history.

(56) References Cited

U.S. PATENT DOCUMENTS

| | | | |
|---|---|---|---|
| 5,465,894 A * | 11/1995 | Clark et al. | 227/175.1 |
| 5,853,422 A | 12/1998 | Huebsch et al. | |
| 6,024,756 A | 2/2000 | Huebsch et al. | |
| 6,117,159 A | 9/2000 | Huebsch et al. | |
| 6,312,446 B1 * | 11/2001 | Huebsch et al. | 606/213 |
| 2003/0199923 A1 * | 10/2003 | Khairkhahan et al. | 606/213 |
| 2004/0094597 A1 | 5/2004 | Whitman et al. | |

(Continued)

FOREIGN PATENT DOCUMENTS

| | | |
|---|---|---|
| EP | 1 836 969 A1 | 9/2007 |
| EP | 1 867 287 A2 | 12/2007 |
| WO | WO 2007/115122 | 10/2007 |
| WO | WO 2008/042229 A2 | 4/2008 |

OTHER PUBLICATIONS

U.S. Appl. No. 12/020,860, filed Jan. 28, 2008, Fredrik Preinitz et al.

(Continued)

*Primary Examiner* — Gregory Anderson
*Assistant Examiner* — Christina Lauer
(74) *Attorney, Agent, or Firm* — Foley & Lardner LLP

(57) ABSTRACT

A medical apparatus (100; 200; 300) is provided, comprising a closure device (21; 102; 202; 302) comprising a first or distal member or portion adapted to be placed on one side of an opening in a wall of a bodily organ, and a second or proximal member or portion adapted to be placed on the opposite side of the opening in the wall of the bodily organ, an insertion assembly (101; 201; 301) comprising at least one actuator operatively connected to at least one of said first or second members, wherein the insertion assembly further comprises at least one motor (105; 106; 205; 306) adapted to maneuver said at least one actuator. In one embodiment the medical apparatus comprises further a closure device (102; 202), which comprises a locking member (130; 230) and a tubular member (121; 221) having two sets of struts (122, 123; 222; 223) being provided with a hinge section, and an insertion assembly (101; 201), which comprises a holder (140; 240) and an actuator, the holder being releasably engaged in the locking member and the actuator being releasably engaged with the tubular member.

17 Claims, 11 Drawing Sheets

(56) References Cited

U.S. PATENT DOCUMENTS

| | | |
|---|---|---|
| 2005/0267523 A1* | 12/2005 | Devellian et al. ............ 606/213 |
| 2007/0027466 A1* | 2/2007 | Ortiz et al. ................... 606/198 |
| 2007/0225756 A1 | 9/2007 | Preinitz et al. |
| 2008/0029574 A1 | 2/2008 | Shelton et al. |

OTHER PUBLICATIONS

U.S. Appl. No. 12/020,877, filed Jan. 28, 2008, Fredrik Preinitz et al.
U.S. Appl. No. 12/020,840, filed Jan. 28, 2008, Fredrik Preinitz et al.
U.S. Appl. No. 12/020,819, filed Jan. 28, 2008, Fredrik Preinitz et al.

* cited by examiner

INSERTION TOOL FOR A CLOSURE DEVICE

FIELD OF THE INVENTION

The present invention relates generally to an insertion tool for a closure device and in particular to such an insertion tool with at least one electrical motor.

BACKGROUND OF THE INVENTION

The closing of an opening in an organ of a patient is a medical procedure that frequently has to be practiced by doctors. The opening may be a hole created by the doctor for a specific and usually temporary purpose, or the opening can be a congenital or acquired defect. An example of the former would be a puncture hole created in a patient's femoral artery to obtain access to the coronary system, while an example of the latter is a septal defect in a patient's heart. For descriptive and illustrative purposes the present invention will be described with reference to such a septal defect, although the techniques described can be applied to other areas of closure of an opening in a bodily organ.

As is well-known, the human heart is divided into four chambers: the left atrium, the right atrium, the left ventricle, and the right ventricle. The atria are separated from each other by the interatrial septum, and the ventricles are separated by the interventricular septum.

Either congenitally or by acquisition, abnormal openings or holes can form between the chambers of the heart, causing shunting of blood through the opening or hole. For example, with an atrial septal defect, blood is shunted from the left atrium to the right atrium, which produces an over-load of the right side of the heart. In addition to left-to-right shunts such as occur in patent ductus arteriosus from the aorta to the pulmonary artery, the left side of the heart has to work harder because some of the blood will recirculate through the lungs instead of going to the rest of the body. The ill effects of such lesions usually cause added strain to the heart with possible ultimate failure if not corrected.

One way to cure a septal defect in the septum of a heart is to position and anchor a specially designed closure device at the septum such that both sides of the septal defect are spanned by the closure device to thereby close the defect. Examples of such septal defect closure devices are known from the U.S. Pat. Nos. 5,853,422; 6,024,756; 6,117,159 and 6,312,446 to Huebsch et al., which disclose a closure device comprising a cylindrical shaft of metal or polymeric material with concentric parallel cuts through the wall of the device to thereby create flattened support struts. The centers of the support struts are intended to move radially away from the longitudinal axis of the device in a hinge-like fashion in response to movements of the proximal and distal ends of the device towards the center thereof. The patents show further a number of different deployment catheters by which the closure device can be positioned and delivered. The deployment catheters are, however, described in a rather rudimentary fashion, and do not seem to include all the members necessary to effect the movements and functions of the closure device.

A similar septal defect closure device is also disclosed in International patent application WO2007/115122 to Callaghan.

SUMMARY OF THE INVENTION

Within the medical field it is of utmost importance that closure devices are positioned correctly and that the insertion tool provides the user with functions that are easy to use and understand. Therefore, a general object of the present invention is to improve a medical apparatus comprising a closure device and accompanying actuator(s) in such a way that a safe and user-friendly medical apparatus is obtained, wherein the movements of the closure device can be controlled in a reliable way by the actuator(s).

In U.S. patent application Ser. Nos. 12/020,860, 12/020,877, 12/020,840, and U.S. Ser. No. 12/020,819, which are assigned to the present assignee and whose entire contents are incorporated herein by reference for the closure devices and methods disclosed therein, a closure device is disclosed for use in closing e.g. a septal defect in a heart or a puncture in a blood vessel. According to embodiments of the present invention, a closure device comprises an elongated essentially tubular member in which a first set of longitudinal slits or cuts have been made on a first side of an uncut central portion and a second set of longitudinal slits or cuts have been made on the opposite side of the central portion. On each side of the central portion, the slits extend towards the ends of the tubular member to terminate a short distance before the respective end, such that uncut proximal and distal end portions are formed. The tubular member, which is made from a flexible and preferably resorbable material, has thereby been provided with proximal and distal sets of struts or ribs. The distal ends of the distal struts are flexibly connected to the distal end portion of the tubular member, while the proximal ends of the distal struts are flexibly connected to the central portion. Similarly, the proximal ends of the proximal struts are flexibly connected to the proximal end portion of the tubular member, while the distal ends of the proximal struts are flexibly connected to the central portion. The struts are further each provided with a hinge section such that each strut in effect is divided into two articulated arms.

When the septal defect closure device during use is compressed such that the distal and proximal end portions are forced towards each other, the hinge sections of the struts move radially out from the longitudinal central axis of the closure device, and the respective arms of the struts assume an essentially perpendicular angle to the central axis of the closure device. The septal defect closure device further comprises a central elongated locking member, which can be either separate from or integrated with the tubular member. In the former case, an elongated locking member is inserted into the tubular member such that the distal end portion of the tubular member abuts one or several radially protruding portions of a distal end of the locking member, and the proximal end portion of the tubular member is then pushed over one or several radially protruding portions of a proximal end of the locking member. The radially protruding portions can comprise a continuous rim or discrete radial protrusions of various dimensions. In the compressed state, the central, proximal and distal portions of the tubular member fit snugly along the central locking member, and the closure device is held in the compressed state by the enlarged distal and proximal rims or other radially protruding portions of the locking member, which prevents the closure device from resuming its original elongated shape. The device further comprises a keying feature, which prevents rotational movement of the locking member in relation to the tubular member.

In accordance with embodiments of the present invention, the insertion tool for a closure device comprises further at least one actuator by which the closure device can be maneuvered through four (4) well-defined configurations: an introduction configuration, a positioning configuration, a closed configuration, and a locked configuration. The actuator comprises an actuating member and at least one holder, whose relative longitudinal translational motion causes the closure device to transform from the introduction configuration via the positioning configuration to the closed configuration, and—if desired—back to the introduction configuration. In a preferred embodiment of the present invention, the actuating member comprises a pusher and a retractor, which move together as a unit to accomplish the first three configurations of the closure device, but which are moved in relation to each other to accomplish the final locked configuration of the closure device.

Furthermore, the insertion tool comprises at least one electrical motor, designed to maneuver the closure device through the four well-defined configurations described above. In one embodiment, the electrical motor(s) of the insertion tool comprises indicators of the present configuration of the closure device as it is moved through the different configurations.

In one embodiment, the medical closure apparatus comprises further a catheter, inside which the mechanical actuator can slide. If the closure apparatus is to be used to close a puncture hole in, for example, a femoral artery, the catheter is preferably replaced with an introducer, which normally has been used during a previous medical procedure and which already is in place in the artery, or is a specially designed introducer.

DETAILED DESCRIPTION OF PREFERRED EMBODIMENTS

The present invention will be described for use with a closure device for a septal defect, such as a patent foramen ovale (PFO). However, it should be noted that it is within the scope of the invention that the present invention be used in placement of other closure devices for bodily openings, such as a closure device for a blood vessel puncture.

Furthermore, the present invention will be described in conjunction with a closure device of an essentially tubular configuration with several struts which fold radially outward when the closure device is compressed lengthwise. However, it is also within the scope of the invention to employ a closure device of other configurations where two components are placed on either side and moved or folded towards each other across the opening to effectively close or seal the opening. The two components can either be separate and held together by a retaining element or be two ends of a multipart device. One such example is a closure device made of thin wire or thread weaved or braided into a netlike tubular structure, which forms two radially expanding discs when the closure device is compressed lengthwise.

When placing a closure device, especially in an atrial or ventricular septal defect, precision and the option to adjust the placement of the closure device is essential for an optimal outcome. Traditionally, insertion assemblies for closure devices are fully manual, i.e. the force and momentum needed to effectuate the movement originates from the user. This can in some cases counteract the reproducibility and reliability of the placement procedure, as different users manipulate the insertion assemblies differently. The present invention provides the user with improved possibilities to effortlessly reposition the closure device any number of times, to ensure best possible closure of the septal defect. Furthermore, the present invention provides the user with enhanced certainty in knowing the exact configuration of the closure device at all times during the procedure.

Figure 1:
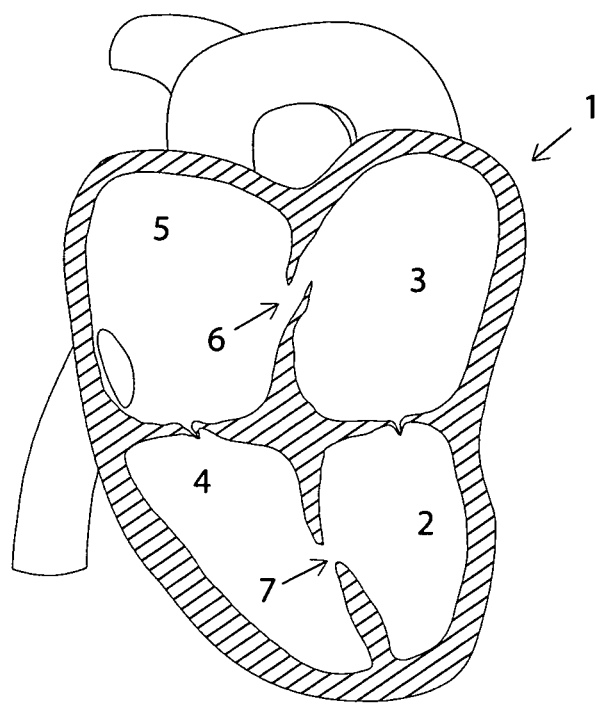
FIG. 1 is a schematic illustration of a human heart having an atrial as well as a ventricular septal defect.

A schematic cross-sectional view of a human heart 1 is shown in FIG. 1. The heart 1, with its left ventricle 2, left atrium 3, right ventricle 4, and right atrium 5, suffers from an atrial septal defect 6 as well as a ventricular septal defect 7. Below a medical procedure will be discussed in which an atrial septal defect is closed. It should, however, be clear that a septal defect closure device according to the present invention equally well could be employed to close a ventricular septal defect such as ventricular septal defect 7 of FIG. 1. It should further be noticed that the septal defects 6, 7 can be accessed from different vessels, e.g. from the superior or inferior vena cava, or from the aorta. This implies, in turn, that throughout the present description terms like "distal" and "proximal" should always be seen from the end of a delivering catheter, through which a septal defect closure device is delivered (and not from any particular chamber or vessel of a heart).

In conjunction with FIGS. 2 to 4, a medical procedure will be briefly described, in which a medical apparatus comprising a septal defect closure device is employed to close a septal defect in the septum of a heart; and thereafter different parts and functions of the closure device itself will be described in detail in conjunction with FIG. 5. The medical apparatus comprises further a motor-driven system of actuators whose operation is described with respect to FIGS. 6 to 11.

Figure 2:
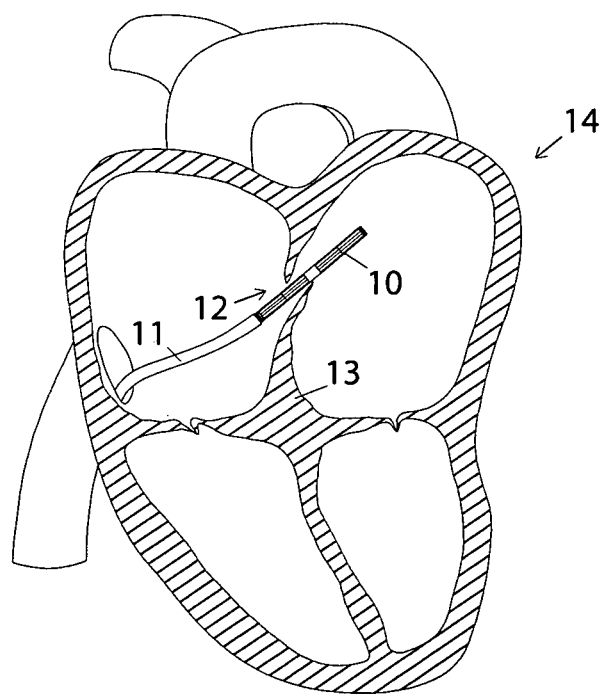
FIG. 2 is a schematic illustration of a human heart having a septal defect, which is to be closed by means of a medical procedure that, in a first step, involves the positioning of a septal defect closure device according to the present invention.

FIG. 2 illustrates a septal defect closure device 10 which by use of a mechanical actuator (not shown in FIG. 2) has been introduced into an atrial septal defect 12 in the atrial septum 13 of a heart 14 using a delivering catheter 11. The closure device 10 is of the same general construction that has been generally described above, and comprises an elongated tubular member in which distal and proximal sets of struts have been provided. The distal struts extend from a central portion of the closure device 10 to a distal end portion thereof, and the proximal struts extend from a proximal end portion of the closure device 10 to the central portion. As already discussed, each strut is provided with a hinge region, and each strut is thereby effectively divided into two hinge-connected arms. In FIG. 2, the closure device 10 is shown in an initial introduction configuration, in which the arms of each strut are substantially aligned with each other. In this introduction configuration, the closure device 10 therefore has a generally elongated tubular shape, which facilitates the introduction of the closure device 10 into the artery and heart of a patient. The introduction configuration is defined as the configuration that the closure device assumes by itself, i.e. without any compression being induced by a mechanical actuator (not shown in FIG. 2) connected to the closure device. In this introduction configuration, the closure device has therefore a generally tubular shape, although the closure device could be pre-formed such that the arms of each strut exhibit a small positive angle in relation to each other. Such a positive angle guarantees the proper radial expansion of the tubular member during longitudinal compression of the tubular member.

To ascertain correct positioning of the closure device 10 with respect to the septal defect 12, the distal set of struts can be moved radially outwards from the central axis of the closure device 10, such that a partly expanded configuration is obtained. The radial movements of the distal struts are effectuated by partially compressing the closure device 10 through the maneuvering of an actuator (not shown in FIGS. 2-4), which in turn is controlled by at least one user-operated motor, which will be described in detail below. In this semi-expanded locating or positioning configuration, the closure device 10 can, if necessary, be retracted until the distal struts abut the distal side of the atrial septum 13 surrounding the septal defect 12. The septal defect 12 can thereby be located by a doctor, who in this phase of the medical procedure will feel a marked increase in resistance against further retraction. This intermediate step of the medical procedure is depicted in FIG. 3. The function and operation of the actuator that effectuates the semi-expanded configuration shown in FIG. 3 are thoroughly explained below. It should be noted that it is within the scope of the invention that a similar locating procedure can be performed by compressing the device such that the proximal struts are expanded, and thereafter advancing the closure device until the proximal struts abut the proximal side of the atrial septum (not shown in the figures), or alternatively by expanding both the distal and the proximal struts.

When the atrial septum 13 and thereby the septal defect 12 have been correctly located, the closure device 10 is fully expanded such that the proximal struts as well as the distal struts are forced radially outwards by maneuvering of the mechanical actuator mentioned above. In this septal defect closing configuration, the closure device 10 spans both the distal side and the proximal side of the septal defect 12, and is then held in this position. As can be seen in FIG. 4, the closure device 10 sandwiches the atrial septum 13 to thereby close the septal defect 12 therein. It should be mentioned that the term "close" or similar terms used herein in conjunction with the description of the closing of a septal defect should not be taken too literally. Such terms are meant to encompass all stages from actually sealing or closing off a septal defect to merely restricting the flow of blood therethrough, the important feature being that the closure device permits and facilitates healing of the septal (or other type of) defect over time. To improve the sealing capability of a closure device of the present type, it is conceivable that the distal and/or proximal struts at least partly are covered by a thin membrane or formed integrally with a thin membrane, which preferably is made from a resorbable material.

Figure 3:
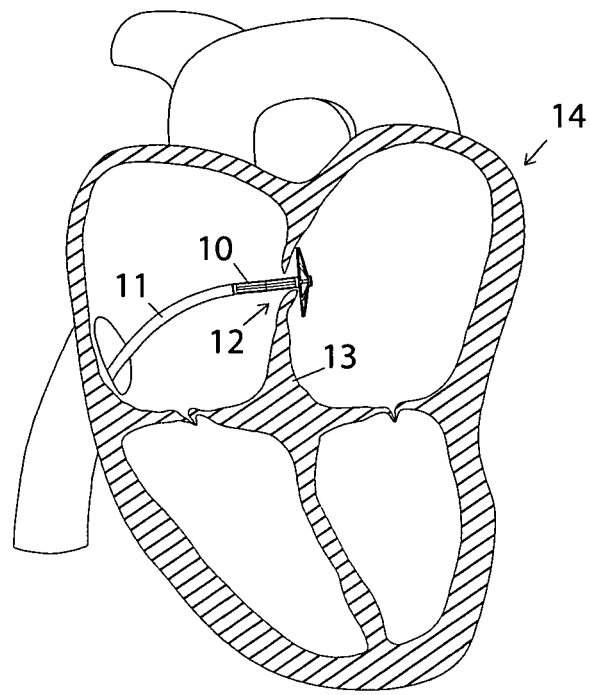
FIG. 3 illustrates an intermediate step in the medical procedure, in which a distal portion of the closure device of FIG. 2 is expanded in order to locate the septal defect from the distal side of the septal defect.
Figure 4:
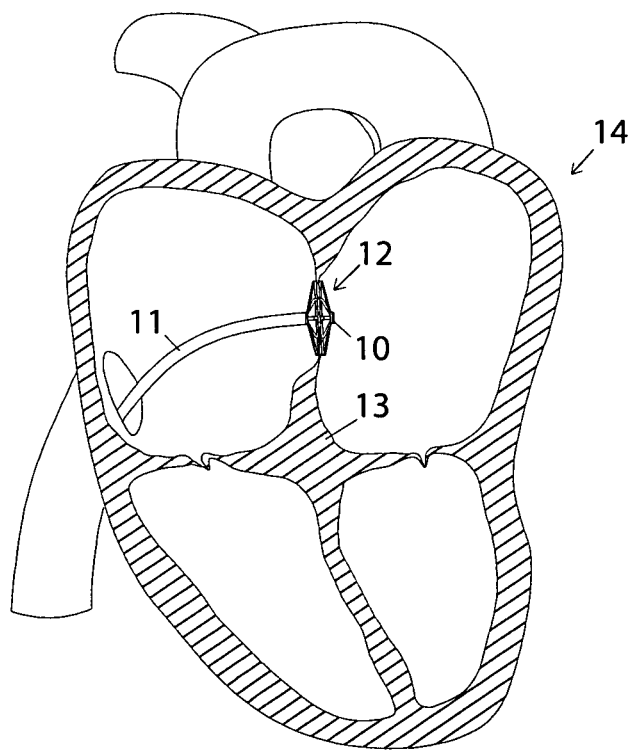
FIG. 4 illustrates the closure device of FIG. 2, which has been positioned in the septum to close the septal defect therein.

A special feature of the closed configuration illustrated in FIG. 4 is that the closure device 10 still is repositionable. This means that by using an actuator (not shown in FIG. 4) controlled by at least one user-operated motor, the closure device 10 is reversibly movable between the configurations described above in conjunction with FIGS. 2-4, i.e. from the closed configuration of FIG. 4, to the intermediate positioning configuration of FIG. 3, and back to the original introduction configuration of FIG. 2. The details of this procedure will be described in detail below. The closure device 10 can then be retracted out of the patient's body and be disposed, or can once again be positioned by repeating the steps illustrated above. The closed configuration of the closure device 10 is defined as the extreme end position of the different and gradually changing positioning configurations. In the closed configuration essentially no further compression of the closure device 10 is possible while still maintaining a reversibly movable closure device 10. The latter will be thoroughly discussed below.

In accordance with the present invention, a closure device encompasses a fourth configuration, in which the closure device is irreversibly locked. The transition from the closed configuration to this locked configuration is effectuated by the actuator mentioned above. A special feature of the present closure device is that a doctor will know when the closed configuration has been reached, so that he or she can decide whether the mechanical actuator should be maneuvered such that the final locked configuration is achieved. Having in mind that the closed configuration constitutes a situation from which the closure device easily can be removed, whereas the locked configuration implies a closure device which needs to be removed surgically, the importance of having a well-defined transition between these two states should be appreciated. Also this feature and how the locked configuration is achieved by a motor-controlled actuator will be further discussed below.

An embodiment of a septal defect closure device 20 according to the present invention is schematically illustrated in FIG. 5, wherein FIG. 5a to FIG. 5e show some of the different configurations discussed in conjunction with FIGS. 2-4. It should be noted that the configurations shown in FIG. 5 are only examples of configurations the device can assume, and a person skilled in the art will realize that during the insertion procedure, the device will move from one configuration to the next, as will be described below.

Figure 5E:
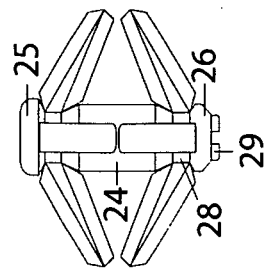
FIG. 5 shows a septal defect closure device according to the invention in five different configurations.
Figure 5D:
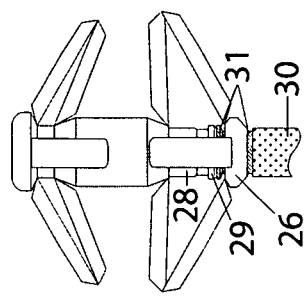
Figure 5C:
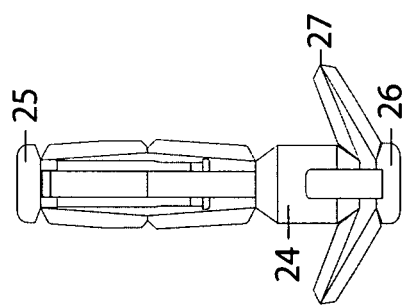
Figure 5B:
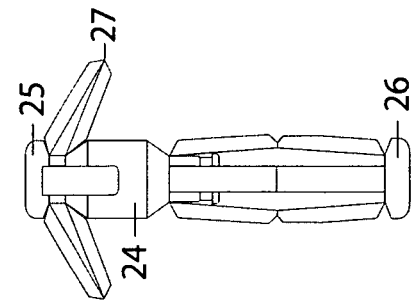
Figure 5A:
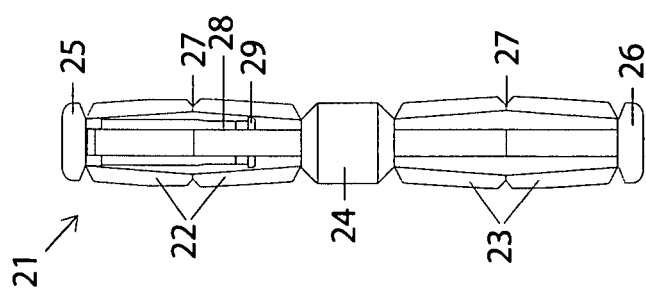

FIG. 5a illustrates the initial introduction configuration, previously mentioned in conjunction with FIG. 2. As previously described, the closure device 21 comprises an elongated tubular member in which distal 22 and proximal 23 sets of struts have been provided. The distal struts 22 extend from a central portion 24 of the closure device to a distal end portion 25 thereof, and the proximal struts 23 extend from the central portion 24 to a proximal end portion 26 of the closure device. As already discussed, each strut is provided with a hinge region 27, and each strut is thereby effectively divided into two hinge-connected arms.

It should further be emphasized that the term "tubular" is merely intended to indicate the general shape of an elongated, hollow member, which comprises a number of struts, the ends of which are connected to ring-shaped or essentially cylindrical members, and which in a first introduction configuration assumes an essentially tubular shape. In other words, a tubular member, like tubular member 21, does not actually have to be cut or slit in order to create distal and proximal struts 22, 23. On the contrary, a tubular member, having struts with hinge regions, as well as ring-shaped or essentially cylindrical central, distal and proximal end portions, can advantageously be directly produced in this form, e.g. by injection molding or die casting. Furthermore, the struts of a tubular member, like tubular member 21, do not have to be exactly aligned with each other. Instead, a tubular member can be preformed in such a way that the two arms of a strut exhibit an angled relation to each other, to thereby guarantee that the arms actually bend outwards during compression of the tubular member (as illustrated in FIG. 5*a*). Nevertheless, the definition of the introduction configuration is still the configuration or state wherein a closure device has not been subjected to any compression by means of a mechanical actuator. The introduction configuration may therefore also be regarded as the "natural" state of the closure device. Furthermore, even though the closure device illustrated in FIG. 5 is shown to have two sets of struts on each half of the device, it should be noted that the number of struts can vary between two and ten or more sets for each half of the device. In addition, the number of struts for each half does not need to equal the number of struts for the other half.

FIGS. 5*b* and 5*c* illustrate the closure device in two different positioning configurations, as discussed in conjunction to FIG. 3. In these configurations, the distal and proximal end portions 25, 26, respectively, of the closure device 21 have been moved towards the central portion 24. The hinge sections 27 have thereby been forced to move outwards from the central axis of the closure device. As a person skilled in the art will recognize, a positioning configuration is also a configuration in which both the distal and proximal end portions have been (partially) expanded, such that an intermediate configuration is achieved. The positioning configuration is defined as all intermediate states between the introduction configuration defined above and the closed configuration, which will be further described and defined below. Movement of different actuators connected to a motor (not shown in FIG. 5) control which configuration the device is maneuvered into. This will be further discussed below.

As can be seen in FIG. 5, the closure device 21 comprises further a locking member 28. The locking member 28, which according to the invention can constitute either a separate or an integrated part of closure device 21, comprises a hollow tubular body, which along the central part of its length is provided with an outer diameter approximately equivalent to the inner diameter of the tubular member. The locking member is further provided with one or several proximal radial protrusions 29, wherein the outer diameter of the radial protrusion(s) is slightly larger than the inner diameter of the proximal end portion 26. During use, the proximal end portion 26 of the tubular member 21, which is made from a somewhat elastic material, must therefore be forced over the proximal radial protrusion(s) 29. This step is achieved when maneuvering the closure device from the closed configuration to the locked configuration, i.e. in the final step of the closure procedure. These steps will be discussed in detail below.

FIG. 5*d* shows one embodiment of a closed configuration, which, as described earlier, is defined as a configuration where the two sets of struts have been expanded and the device compressed as much as possible without moving into the locked configuration. This is a configuration where further compression of the tubular member 21 is not possible—unless extra force is applied such that the proximal end portion 26 of the closure device is forced over the proximal end rim 29 of the locking member. In the present invention, as will be further discussed below, the movements of the closure device are effectuated by at least one motor, which in turn moves the different parts of the closure device with a system of actuators. By moving the different actuating members back and forth, a doctor can during a preceding positioning operation let the tubular member 21 assume different positioning configurations, to thereby locate a septal defect (or some other type of tissue opening, e.g. a percutaneous puncture in an artery wall) and position the closure device 21 in the opening of the defect. The different actuators will be described in detail below; however, here it suffices to mention a pusher 30 and a retractor 31, and a holder (not seen in FIG. 5). The holder extends within the entire assembly, and attaches to the distal end of the locking member 28. In the situation illustrated in FIG. 5*d*, the distal end of the retractor 31 abuts the proximal end rim 29 of the locking member 28. Thus, FIG. 5*d* illustrates a well-defined end position for the positioning operation, in which no further compression of the tubular member 21 is possible by maneuvering of the actuating member in relation to the holder without forcing proximal end portion 26 over proximal end rim 29. If, on the other hand, an actuating member were engaged inside a proximal end portion of a tubular member, a well-defined end point of the positioning operation would be when a proximal end portion of the tubular member abuts a proximal end rim of a locking member, i.e. a configuration in which no further compression of the tubular member is possible without forcing an end portion over an end rim. The closed configuration of a closure device according to the present invention is thereby defined as the extreme end position of the positioning configurations, wherein an end portion of a locking member prevents further compression of a tubular member.

From FIG. 5*d* it may be realized that when the retractor 31 abuts the proximal end rim 29 of the locking member 28, the closure device 21 can be transferred into the final locked state by movement of the pusher 30. To accomplish this, the pusher 30 (which can slide with respect to retractor 31) is advanced, so that the proximal end portion 26 of the tubular member 21 is forced up and over the proximal end rim 29 of the locking member 28. This movement requires that the proximal end portion 26 and/or the proximal end rim 29 possesses a certain degree of resilience.

The final locked configuration of the closure device 21 is illustrated in FIG. 5*e*, in which the distal and proximal end portions 25, 26 of the tubular member 21 have been fully moved towards each other until the central portion 24 is positioned centrally over the locking member 28 and the proximal end portion 26 has been moved over the proximal end rim 29 of the locking member 28. The closure device 21 is held in this compressed state due to the enlarged distal and proximal end rims of the locking member 28, which have diameters larger than the distal end portion 25 and the proximal end portion 26, respectively. The closure device 21 can then be released and left in this locked configuration by maneuvering of further actuating members described below. The locked configuration of a closure device is thereby defined as the configuration in which the closure device is fully expanded, and in which the closure device can be held without assistance of an actuator.

Figure 6:
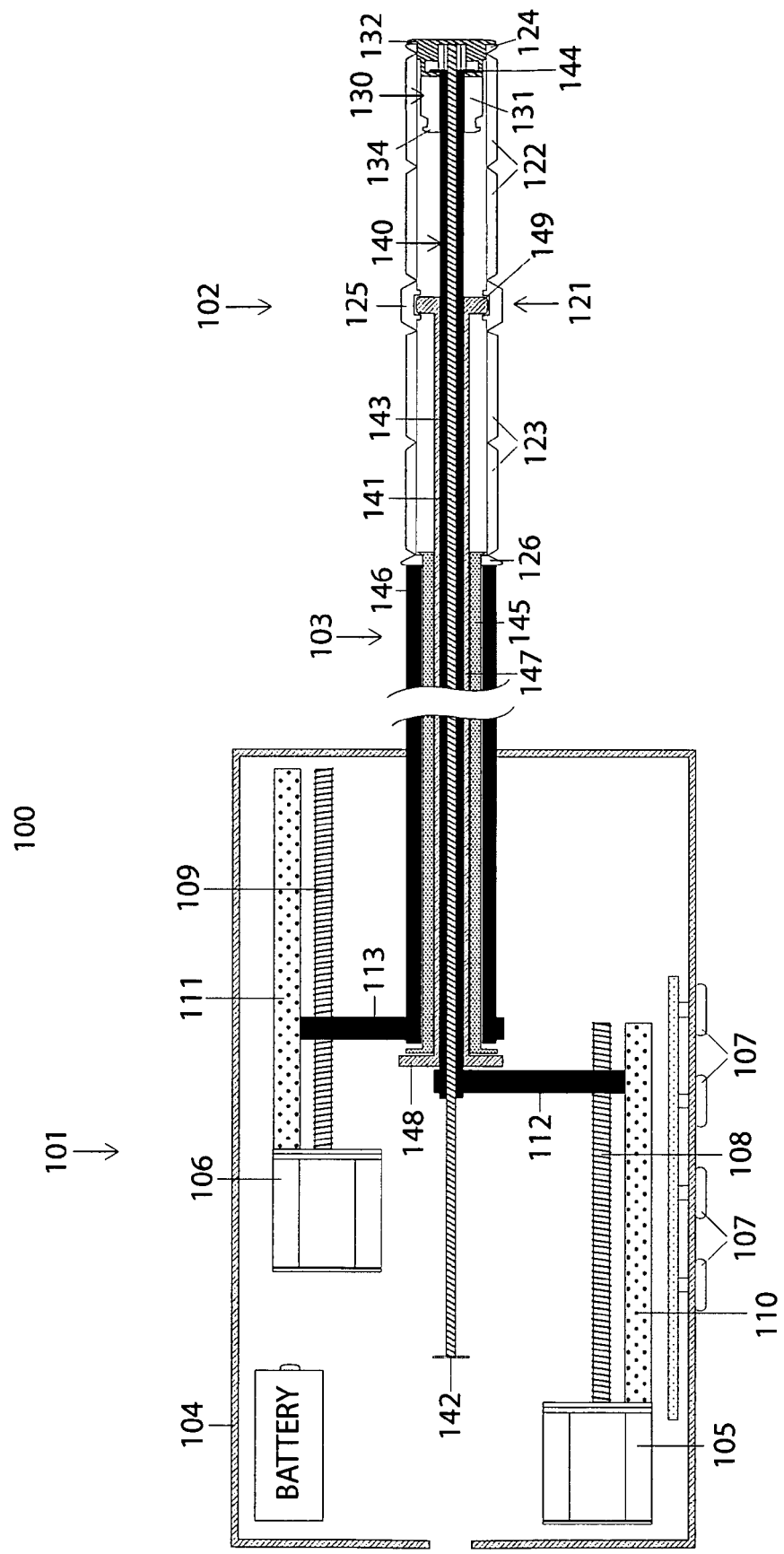
FIG. 6 is a sectional drawing of a medical apparatus according to the present invention shown in an introduction stage of a closure delivering operation.

FIG. 6 illustrates a medical apparatus 100 comprising a motor-driven insertion and delivery assembly 101, a closure device 102, and a delivering shaft 103. Preferably, the delivery of the device to the closure site is performed with the delivering shaft 103 and closure device 102 initially placed within a catheter (not shown in the Figures) which is used to insert the device into the body and deliver the distal part of the assembly to the closure site. Upon arrival in the heart (or other organ) the catheter is withdrawn to a position proximally of the entire closure device before initiation of the closure procedure itself. The closure device 102 is of the same general design that has been described above, and comprises an elongated tubular member 121 and a locking member 130. The tubular member 121 comprises a first or distal set of struts 122, which extend from a first or distal portion 124 of the tubular member 121 to a central portion 125 thereof. The tubular member 121 comprises further a second or proximal set of struts 123, which extend from the central portion 125 to a second or proximal portion 126 of the tubular member 121. The locking member 130 comprises a hollow tubular body 131, a distal end rim 132, and a proximal end rim 134. The body 131 of the locking member 130 is generally hollow, except for its most distal portion which is solid to avoid leakage of blood through the locking member 130. The proximal half of the locking member has been split lengthwise, creating a slit or opening to accommodate a central holder in later stages of the closure procedure (further described below).

The insertion assembly 101 comprises a housing 104, a first electrical motor 105, and a second electrical motor 106. The electrical motors are connected to a battery by means of electrical cables (not shown in the Figures). The insertion assembly housing 104 is illustrated in FIG. 6 as a rectangular box. However, it should be noted that the insertion assembly housing can be of any shape, such that the components described below fit within the housing and the different procedural steps can be performed. For instance, the housing can have a cylindrical or curved shape, preferably providing the user with a comfortable surface for handling. The housing is further provided with buttons 107, to enable the user to move the closure device through the different configurations during positioning of the device. The buttons 107 are here illustrated as being four pushbuttons, however this is simply illustrative. How the user maneuvers the insertion device 101, and the corresponding buttons, levers or sliders needed, will be described in detail further below.

The distal portion 124 of the tubular member 121 has been threaded onto the hollow body 131 of the locking member 130, and abuts the distal end rim 132 of the locking member 130. The closure device 102 is connected to the insertion assembly 101 by a distal holder 140 and a central holder 147. The distal holder 140 comprises a locking pin 141, a locking pin handle 142, and a tubular distal holder member 143. The distal end of the distal tubular holder member 143 is cut and bent outwards into two grip members 144, which are engaged in a recess or cavity in the interior of the hollow body 131 of the locking member 130. The grip members 144 are prevented from approaching each other, i.e. being squeezed together, by the locking pin 141, which in this stage of a delivering operation is disposed within the tubular holder member 143. As will be further elucidated below, except for in the last stage of a delivering operation, when the closure device is to be released, the locking pin 141, and the tubular distal holder member 143 (collectively the distal holder member 140) move together as a unit in response to reciprocal movements of the actuators connected to the motor(s) (further described below).

The central holder 147 comprises a hollow elongated member, with the distal holder member 140 slidably engaged within. The distal end 149 of central holder 147 is enlarged and engaged in a recess or cavity inside central portion 125 of the tubular member 121. The enlarged end 149 of the central holder 147 is preferably shaped such that it will easily slide within the locking member 130 in later stages of the closure procedure. This will be described in detail below. The proximal end 148 of central holder 147 is fixedly attached or integrated within the housing 104 of insertion assembly 101. Thereby, until release of the central holder 147 from the closure device 102, the central portion 125 of the closure device 102 is located at the same distance from the insertion assembly 101, providing a secure reference point when maneuvering the closure device through the different configurations during placement of the closure device within the opening. This enables the user to position and maintain the central portion 125 of the closure device 102 in the opening to be closed while maneuvering the two sets of struts 122, 123.

The delivering shaft 103 further comprises a tubular retractor 145, slidably arranged outside the central holder 147, and a tubular pusher 146, slidably arranged outside the tubular retractor 145. The distal end of the tubular retractor 145 is upended; and the proximal portion 126 of the tubular member 121 is fixedly arranged between the upended distal end of the retractor 145 and the distal end of the pusher 146. As will be further elucidated below, except for in the penultimate stage of a delivering operation, the retractor 145 and the pusher 146 move together as a unit in response to reciprocal movements of the actuators connected to the motor(s) (further described below).

Since the tubular member 121 is fixated at three points; i.e. at the pusher 146 at one end, at the distal portion of the locking member 130 at the other end, and at the central portion 125 by central holder 147, the relative motion between the holder 140, the pusher 146 and the central holder 147 causes the distal or proximal part of the tubular member 121 to compress or expand longitudinally.

Each motor 105, 106 is provided with a drive shaft 108, 109, each supplied with external threads and a corresponding gauge 110, 111. The latter is used to indicate or sense the longitudinal position of a moving beam 112, 113 mounted on the corresponding drive shaft 108, 109. Each moving beam 112, 113 is mounted on the corresponding drive shaft 108, 109 by threading the drive shaft through a longitudinal opening in the moving beam. This opening is supplied with internal threads matching those of the drive shaft. In operation, each motor 105, 106 will rotate its corresponding drive shaft 108, 109 such that the corresponding moving beam 112, 113 will move up or down the drive shaft.

The moving beam 112 is fixedly attached to the proximal end of the distal tubular holder member 143. As mentioned before, the locking pin 141 is slidably mounted within the distal tubular holder member 143, and protrudes proximally of the moving beam 112, ending in locking pin handle 142. The moving beam 113 is fixedly attached to the proximal end of pusher 146.

Figure 7:
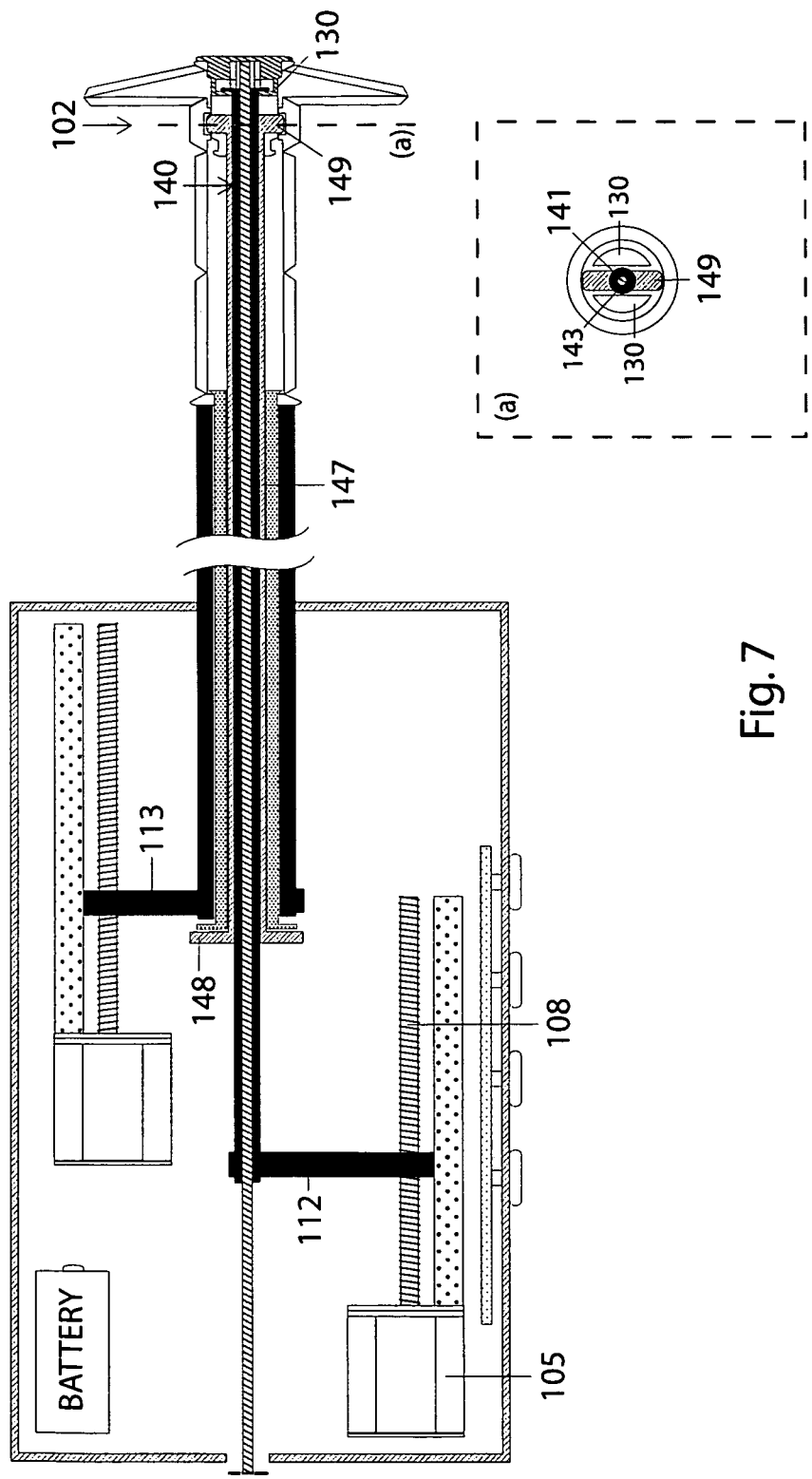
FIG. 7 is a sectional drawing of the medical apparatus of FIG. 6 shown in a positioning stage of the closure delivering operation.
Figure 8:
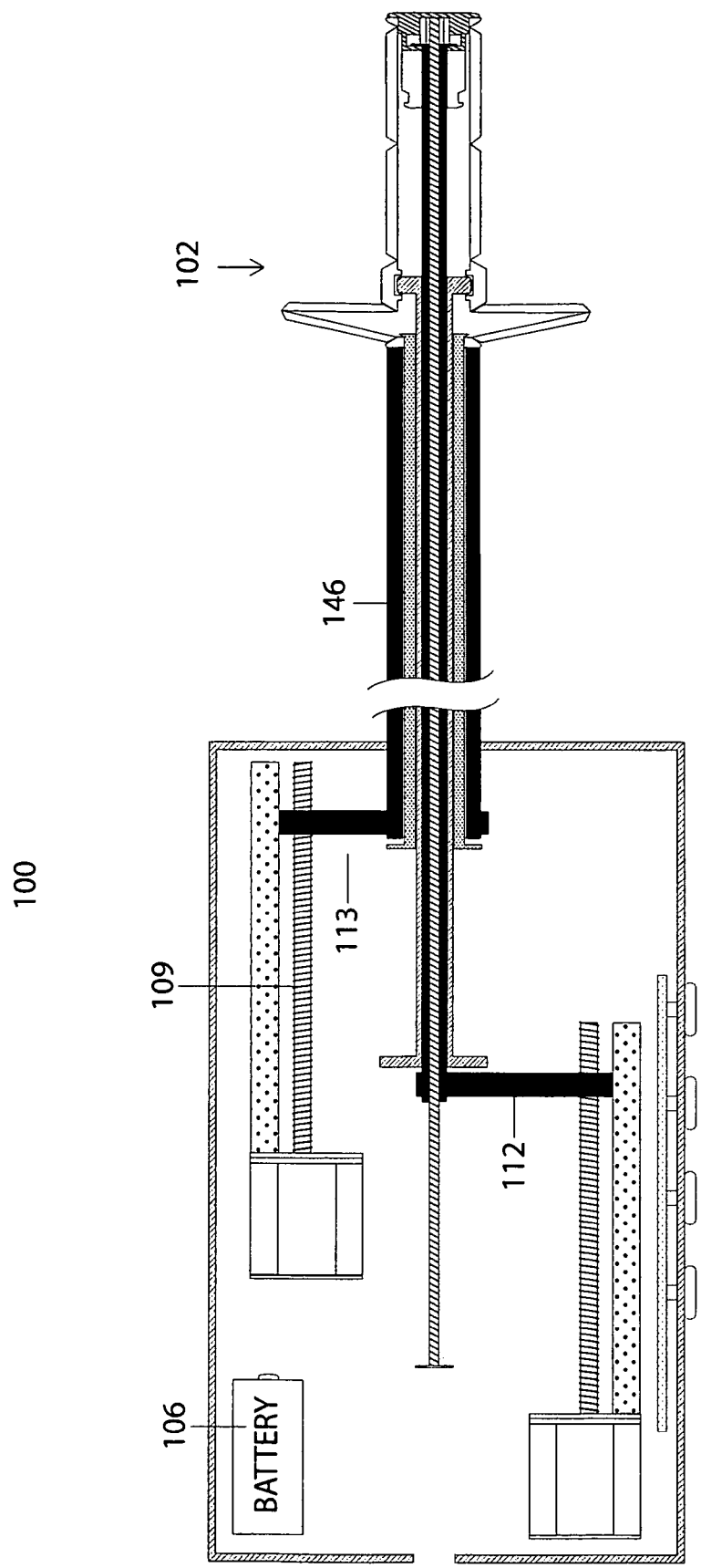
FIG. 8 is a sectional drawing of the medical apparatus of FIG. 6 shown in another positioning stage of the closure delivering operation.

In FIG. 6 the medical apparatus 100 is shown in an introduction phase. In this phase, the moving beams 112, 113 are both in a position adjacent to the attachment point 148 of central holder member 147, which corresponds to a fully elongated closure device. To proceed from the introduction configuration of FIG. 6 to a positioning configuration as described above, either one or both of the moving beams 112, 113 are moved away from the central position. When motor 105 is activated to rotate drive shaft 108, such that moving beam 112 will move proximally, the distal holder 140 will also move proximally, thereby compressing the distal half of the closure device 102. The end position of this configuration is shown in FIG. 7. On the other hand, when the medical apparatus 100 is in the introduction phase shown in FIG. 6, activating motor 106 to rotate drive shaft 109 such that moving beam 113 will move distally and push on pusher 146, results in compression of the proximal half of the closure device 102. The end position of this configuration is shown in FIG. 8. As mentioned, these two actions can be performed separately, or simultaneously. Furthermore, each action can be performed partially, in fact to any desired degree. Thus, the user can easily manipulate each half of the closure device to any desired positioning configuration, to thereby locate a septal defect (or some other type of tissue opening, e.g. a percutaneous puncture in an artery wall) and thereby optimally position the closure device 102 in the opening of the defect.

It should be noted that as the closure device 102 is compressed, the locking member 130 will at some point be even with the enlarged portion 149 of the central holder member 147 (for example in the configuration of FIG. 7). To accommodate both parts within the tubular member 121, the enlarged end portion 149 has such a shape that it will fit within the lengthwise split in the proximal half of the locking member 130. One solution is illustrated in the cut-through figure (a) in FIG. 7, where the locking member 130 and the enlarged portion 149 of the central holder member are shown from a proximal direction along the longitudinal axis of the insertion assembly 100, at a cut-through point (a) indicated in FIG. 7. The location of the tubular distal holder member 143 and the locking pin 141 are also indicated.

Figure 9:
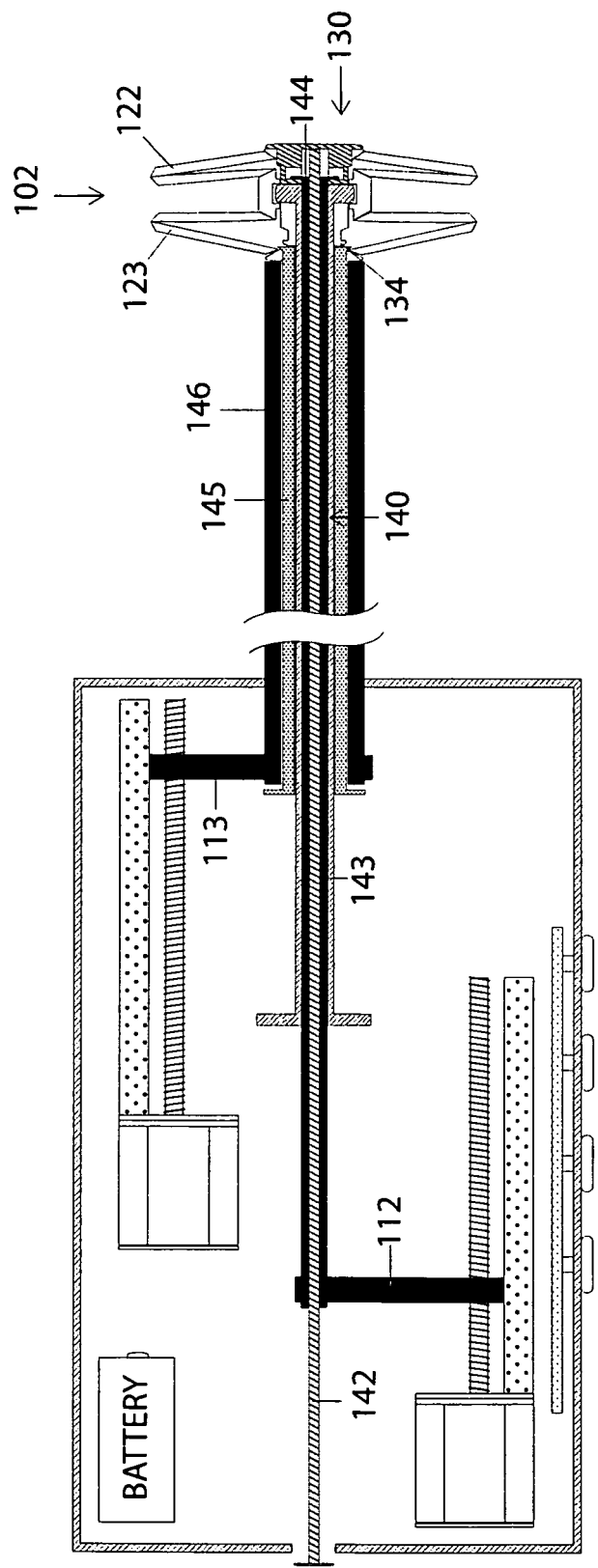
FIG. 9 is a sectional drawing of the medical apparatus of FIG. 6 shown in a closing stage of the closure delivering operation.

During the positioning procedure, the closure device 102 is compressed such that the tissue wall is sandwiched between the distal struts 122 and the proximal struts 123 of the tubular member 121 (as illustrated in FIG. 4). The closed configuration of the closure device 102 is depicted in FIG. 9, which shows that the distance between the two moving beams 112, 113 has been increased compared to the configurations of FIGS. 6-8, which, in turn, means that the distance between the distal end of the holder 140 and the distal end of the pusher 146 has been reduced. This has caused both the distal struts 122 and proximal struts 123 to assume an essentially perpendicular angle to the central axis of the closure device 102. In FIG. 9 it should in particular be noted that the closure device 102 still is fixedly arranged between the holder 140 and the pusher 146, which means that the whole procedure can be reversed and repeated from any previous stage. In other words, by reversing the movement of the moving beams 112, 113, either together or separately, and thereby decreasing the distance between the two moving beams 112, 113, the closure device 102 can again be transformed to the delivering configuration illustrated in FIG. 6, and the whole medical apparatus 100 can be retracted out of a patient's body and be disposed, or the steps shown in FIGS. 7 and 8 could be repeated in order to reposition the closure device 102 in an opening or defect in an organ.

If the user determines that the closure device 102 is correctly positioned in an opening or defect in an organ, and, consequently, that the delivering operation described in conjunction with FIGS. 6, 7 and 8 has been successful, he or she may decide to irreversibly leave the closure device 102 in the organ, to permanently close the opening or defect therein. To this effect, the closure device 102 has to be transferred from the closed configuration of FIG. 9 to a locked configuration, illustrated in FIG. 10. Here it should be noted that in FIG. 9 the distal end of the retractor 145 abuts the proximal end rim 134 of the locking member 130; and, since the inner diameter of the tubular retractor 145 is smaller than the diameter of the proximal end rim 134 of the locking member 130, the retractor 145 cannot be advanced any further in relation to the grip members 144 at the distal end of the holder member 143.

Figure 10:
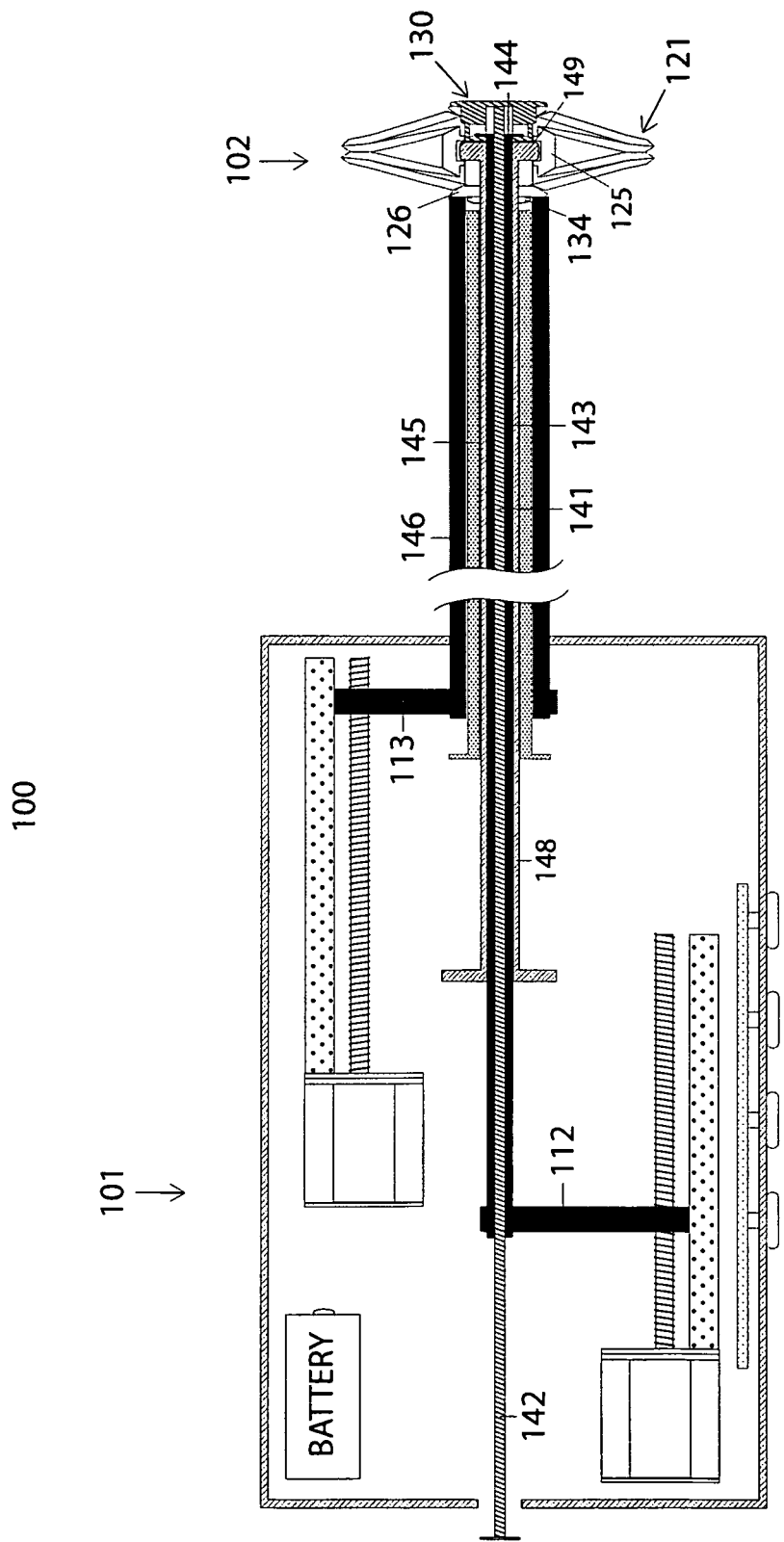
FIG. 10 is a sectional drawing of the medical apparatus of FIG. 6 shown in a locking stage of the closure delivering operation.

FIG. 10 illustrates the medical apparatus 100 in a configuration in which the closure device 102 is irreversibly locked. By comparing FIG. 9 and FIG. 10 it can be noted that the distance between the two moving beams 112, 113 has been slightly increased in the locked configuration of FIG. 10 compared to the closed configuration of FIG. 9, which means that the pusher 146 has been moved closer to the distal end of the holder member 143. As was explained above, the retractor 145, which is slidably arranged in the tubular pusher 146, can, however, not be moved any closer to the distal end of the holder member 143, resulting in the pusher 146 pushing the proximal portion 126 of the tubular member 121 over the proximal end rim 134 of the locking member 130. In this stage of a delivering operation, the retractor 145 and the pusher 146 no longer move in common as a unit, instead it is the relative motion between the pusher 146 and the retractor 145 that accomplishes the transition from the closed configuration of FIG. 9 to the locked configuration shown in FIG. 10.

It should here be noted that the insertion assembly is preferably provided with a safety mechanism, preventing the user from accidentally moving the closure device from a closed to a locked configuration prematurely. It may be appreciated that this feature is particularly advantageous, because—as has been emphasized before—the closed configuration represents a reversible state from which the closure device 102 can be reversibly operated by the mechanical insertion and delivery assembly 101, whereas the locked configuration is a state from which the closure device 102 cannot be retrieved from a patient's body, at least not without an extensive medical intervention, and the possibility of an unintentional locking of the closure device 102 should therefore be avoided.

Figure 11:
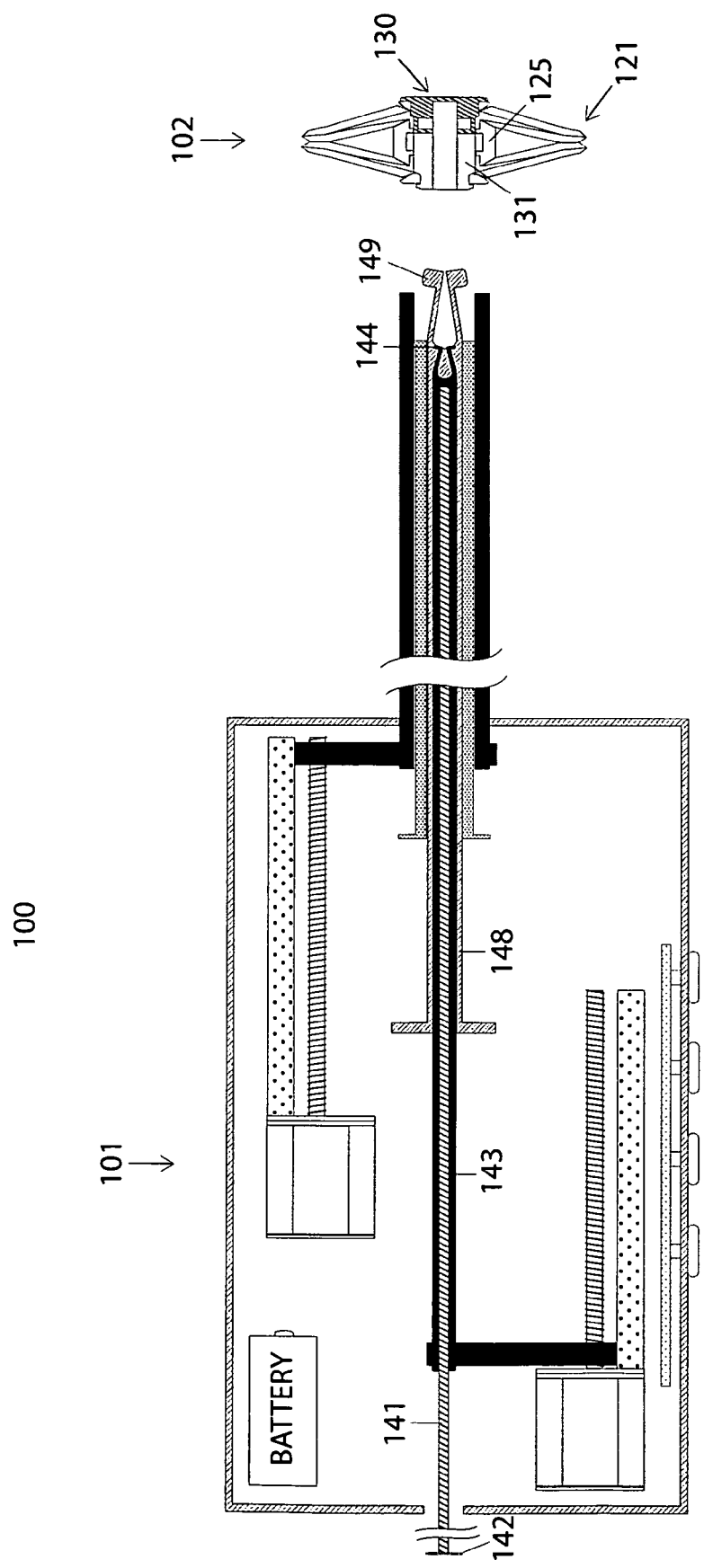
FIG. 11 is a sectional drawing of the medical apparatus of FIG. 6 shown in a releasing stage of the closure delivering operation.

The last important operation that a doctor carries out is to release the closure device 102 from the insertion assembly or tool 101. This is done by retracting the locking pin handle 142 in relation to the holder member 143, i.e. the locking pin 141 is moved relative to the holder member 143. More specifically, by retracting the locking pin handle 142 such that the locking pin 141 is withdrawn proximally of the grip members 144 at the distal end of the holder member 143 and also proximally of the enlarged end 149 of the central holder 148, both the grip members 144 and the two halves of the enlarged end 149 are free to approach each other; and, in response to a retracting movement of the entire mechanical insertion tool 101, the grip members 144 are disengaged from the recess or cavity in the interior of the hollow body 131 of the locking member 130, and enlarged end 149 is disengaged from the recess in the central portion 125 of the tubular member 121. FIG. 11 illustrates how the closure device 102 is released from the insertion assembly 101, and illustrates further that the grip members 144 were preformed with a tendency to point towards each other. Similarly, without the locking pin present, the two halves of the enlarged end 149 of the central holder 148 are also free to bend inwards, as these also have been preformed with a tendency to point inwards. Optionally, an insertion assembly, like insertion assembly 101, may be provided with a safety mechanism that prevents the withdrawal of a locking pin before two moving beams have been moved to their outmost position with respect to each other, to avoid the risk of unintentionally disengaging a closure device from an insertion assembly.

Figure 12:
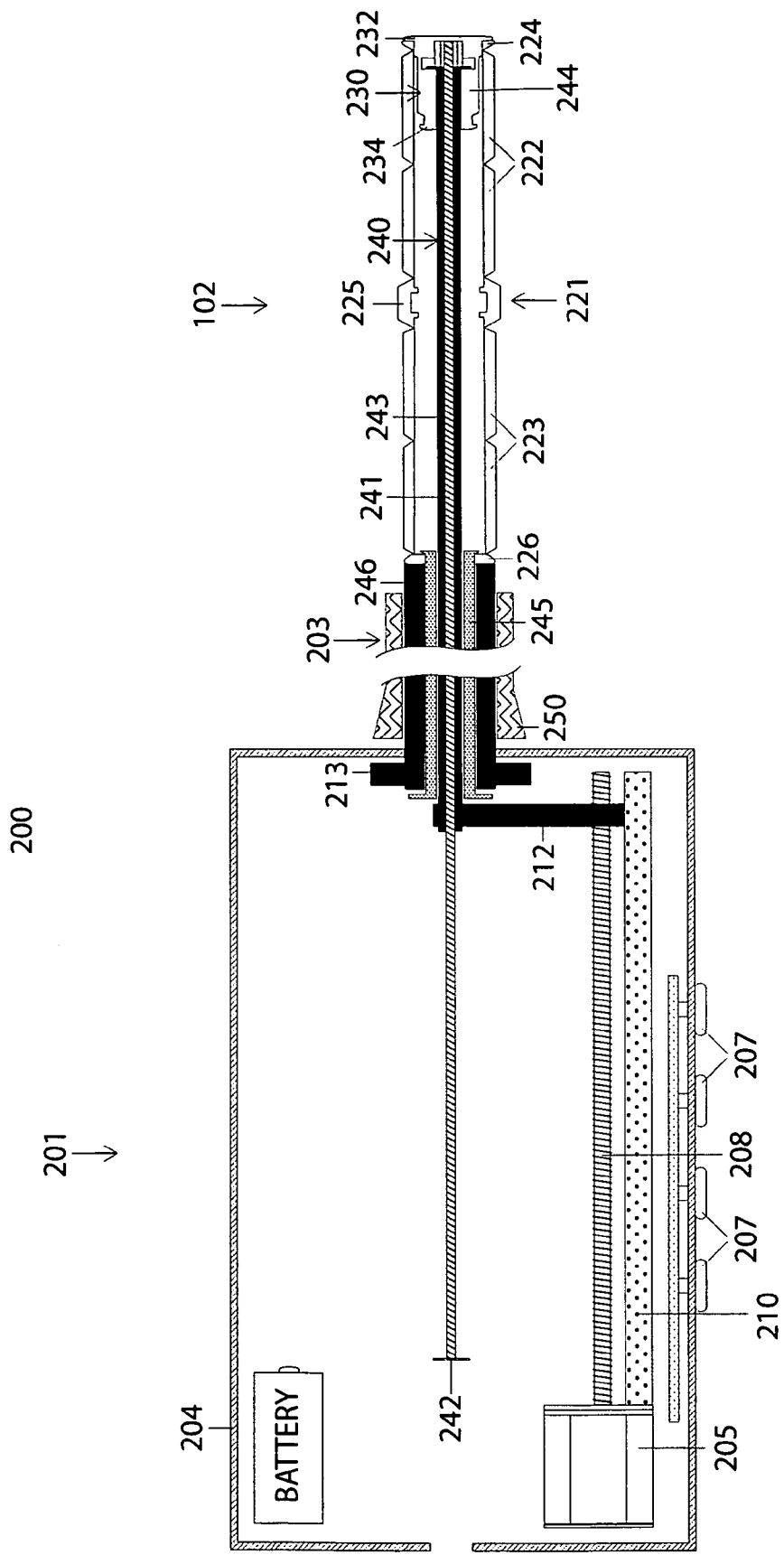
FIG. 12 is a sectional drawing of a medical apparatus according to another embodiment the present invention shown in an introduction stage of a closure delivering operation.

In another embodiment, illustrated in FIG. 12, the insertion assembly comprises only one motor to maneuver the closure device through the different configurations. This embodiment is similar to that described above, except that it only comprises one motor, does not have a central holder member, and optionally further makes use of the delivery catheter enclosing the delivery shaft and closure device to help maneuver the closure device. As mentioned above, initially, the delivery shaft 203 and closure device 202 can be enclosed in a catheter 250 to ease insertion into the organ of interest. In the present embodiment, comprising only one motor, this catheter is further used to control which part of the closure device is expanded in the different procedural steps, as will be described in detail below. The motor 205 is here provided with a drive shaft 208 and a corresponding gauge 210. As in previous embodiments, the latter is used to indicate or sense the longitudinal position of a moving beam 212 mounted on the drive shaft. As described in previous embodiments, the moving beam 212 is mounted on the drive shaft 208 by threading the drive shaft 208 through a longitudinal opening in the moving beam 212. The opening is supplied with internal threads matching those of the drive shaft. In operation, the motor 205 will rotate the drive shaft 208 such that the moving beam 212 will move up or down the drive shaft 208.

The moving beam 212 is fixedly connected to the tubular distal holder member 243. In the present embodiment, the proximal end 213 of a tubular pusher 246 is fixedly attached inside the housing 204 of the insertion assembly 201. This provides a fixed reference point during the closure procedure, such that the distance from the external insertion assembly 201 and the proximal end of the tubular closure device 221 remains the same throughout the procedure, up until the closure device is to be locked and released. Furthermore, a tubular retractor 245 is slidably mounted within the pusher 246. As in previous embodiments, the distal end of the tubular retractor 245 is upended; and the proximal portion 226 of the tubular member 221 is fixedly arranged between the upended distal end of the retractor 245 and the distal end of a tubular pusher 246. As will be further elucidated below, except for in the penultimate stage of a delivering operation, the retractor 245 and pusher 246 remain together as a unit. It should be noted that the proximal end of the retractor 245 is not fixedly mounted to any part of the insertion assembly 200.

In the introduction configuration, the moving beam 212 is adjacent to the attachment site 213 of the tubular pusher 246, i.e. in the most distal position possible on the drive shaft 208. To compress the closure device 202, the moving beam is moved proximally, thereby causing a pulling motion on the distal holder member 243, causing the distal 222 and/or proximal struts 223 to move radially outwards, as in previous embodiments. If the delivery catheter 250 is positioned to cover the proximal half of the closure device, only the distal struts 222 will expand. However, if the delivery catheter 250 is withdrawn to a position proximal of the closure device 202, both sets of struts, 222, 223 will expand simultaneously. The position of the delivery catheter 250 is manually controlled by the user.

The moving beam 212 is moved proximally until a closed configuration of the closure device 202 is achieved (as illustrated in FIG. 5d). Referring back to FIG. 12, and similarly to the previous embodiment in FIG. 9, a closed configuration is a configuration where the device cannot be further expanded without pushing the proximal end 226 of the closure device over the proximal rim 234 of the locking member 230. As in previous embodiments, until this stage, the closure procedure is fully reversible at any stage, and can even be completely reversed until the introduction configuration is achieved, whereupon the entire assembly can be retracted from the site and removed from the patient. Preferably, the insertion assembly is provided with a safety mechanism to prevent premature maneuvering of the closure device from the closed to the locked configuration.

Once the user is satisfied with the placement of the closure device, moving beam 212 is moved the final step proximally on the drive shaft 208. Just as was described in the previous embodiment in conjunction with FIG. 9 and FIG. 10, since the proximal rim 234 of the locking device 230 abuts the retractor 245 in the closed configuration, further pulling motion on distal holder member 241 will cause pusher 246 to push the proximal portion 226 of the tubular member 221 over the proximal end rim 234 of the locking member 230, thereby achieving the locked configuration of the closure device.

Release of the closure device is performed as in earlier embodiments. By retracting the locking pin 241 by pulling proximally on handle 242, the grip members 244 will be allowed to approach one another, and the closure device 202 released from the insertion assembly 201.

It should be noted that the term motor, as used herein, comprises any type of motor, such as, but not limited to, electrical motors including battery-powered motors, and motors powered by compressed gas such as carbon dioxide or air. In the present invention the motor is preferably a battery-powered electrical motor.

The advantages of using an embodiment with one motor are that it is a simpler model to manufacture, both in terms of time and complexity, and needs less power and user effort during use. On the other hand, using an embodiment with two motors has the advantage of the user being able to control each half of the closure device separately.

In order to operate the motor(s) of the previously described embodiments several options are available. In some embodiments, when using either one or two motors, each motor is operated separately by a button or lever 107, 207 with two different settings, one for bringing the struts into an expanded configuration and one for bringing the struts into an elongated configuration. In an embodiment with two motors, each motor can control a separate set of struts, so using separate buttons enables independent maneuvering of each half of the closure device. In addition, the insertion assembly is provided with buttons for locking of the closure device and for release of the closure device from the insertion assembly. Preferably, the insertion device is provided with means, such as e.g. a catch or spring being released, to ensure that locking cannot be performed until the device is fully closed and preferably also so that the user needs to verify that locking is to be performed. A non-limiting example of the latter would be a catch which has to be released by the user before performing the final locking step. Furthermore, it is preferable that the insertion device be provided with means, to ensure that release cannot be performed until the closure device has been locked. A non-limiting example is a releasable catch or spring which the user has to activate in order to be able to pull back the locking pin.

In another embodiment, the buttons or levers that operate each motor are provided with several distinct settings, i.e. separate indications of the closure device being maneuvered into, for example, an elongated, semi-elongated or fully expanded configuration. In a further embodiment, each motor can be operated by a sliding lever, enabling the user to smoothly move each half of the closure device into any degree of expansion.

In a further embodiment the operation of the motor(s) is regulated via a programmable chip, using any of the described configurations of buttons or levers above, or any other configuration known in the art. Furthermore, the insertion assembly can be provided with an analog or digital display, to indicate the present configuration of the closure device. This can facilitate use and confirm each step to the user during the closure procedure, increasing user confidence during use. By using a programmable chip, the device can preferably be provided with the safety mechanisms mentioned above by incorporating confirmation steps in the programming itself.

Figure 13:
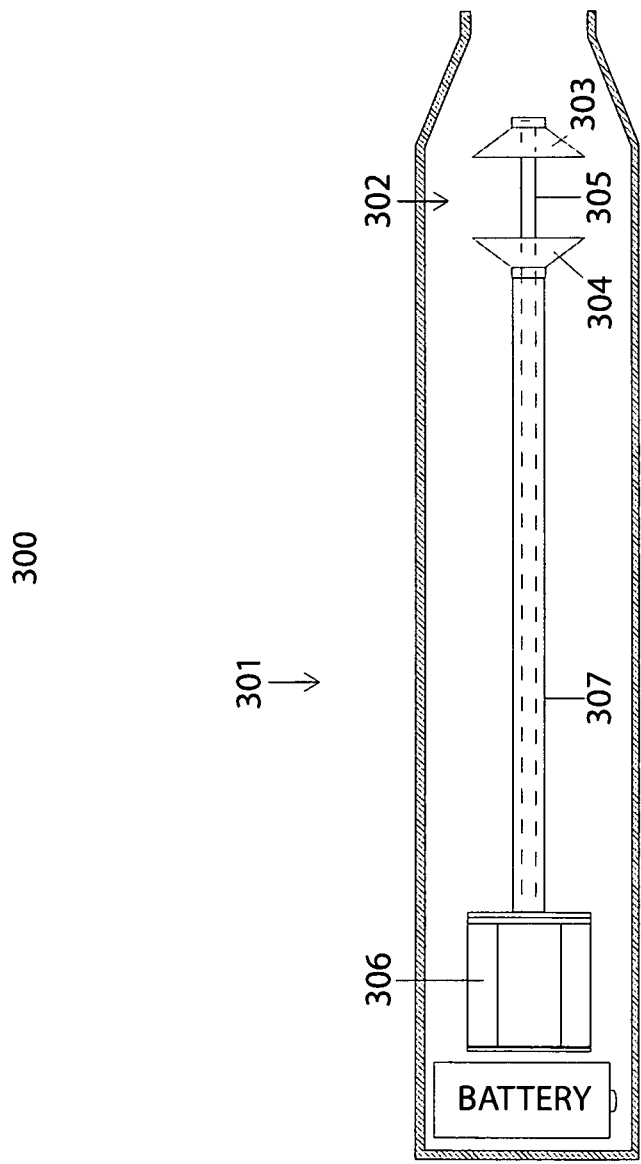
FIG. 13 is a sectional drawing of a medical apparatus according to a further embodiment the present invention.

As mentioned earlier, an insertion tool can be designed for placement of a medical device for the closure of a blood vessel puncture. In one embodiment, as illustrated in FIG. 13, a closure device 302 comprises a first closure member 303 and a second closure member 304, connected to each other by a retaining element 305, e.g. a suture or a stem. In an insertion assembly 300 the closure device is initially operatively connected to a motor 306 by at least one actuator 307. The motor 306 is designed to drive the actuator in one or several of the steps in insertion of the closure device into a blood vessel puncture and thereby seal the opening.

It should be apparent to a person skilled in the art that the use of a motor in placing a closure device depends on the type of closure device provided. In a further embodiment a motor is coupled to a tamping tube, thereby controlling the advancement of the tamping tube in order to move a first closure member into a position adjacent to a vessel puncture and on the opposite side of a vessel puncture compared to a second closure member. In another embodiment, if a closure device comprising two closure members connected to each other by e.g. a suture or filament is provided, the suture itself can act as an actuator in pulling the first closure member towards the second closure member across the opening. Furthermore, in the latter case, a separate pulling actuator can be provided.

An advantage of using motor(s) to control the movement of the closure device is that the amount of force and/or speed can be preset, either when manufacturing the insertion assembly or by the user, such that the force applied to the closure site can be adapted to ensure proper closure while inflicting minimum damage to the closure site.

In a further embodiment, an insertion tool provided with either a single motor for tamping of a closure device at a vessel puncture site, or one or several motors for placing a closure device at a septal defect, can comprise indicator measures to aid the user in following and moving between the different procedural steps in placing the closure device (e.g. as described in conjunction with FIGS. 2 to 4). The indicator measures can comprise light signals, sound signals, a digital or analog display, or a combination of the above. For an insertion tool designed for placement of a closure device in a blood vessel puncture, the indicator preferably specifies the amount of force applied to the tamping tube, either by indication on a pre-defined scale or by displaying characters. For an insertion tool designed for placing a closure device at a septal defect, one embodiment comprises an indicator which displays the current configuration of the closure device by symbols, lights and/or sounds. The configurations indicated are preferably those described previously, i.e. an introduction configuration, a positioning configuration, a closed configuration, and a locked configuration. In another embodiment, the indicator specifies the percentage of expansion of either one or both of the two ends of the closure device.

Although the present invention has been described with reference to specific embodiments, also shown in the appended drawings, it will be apparent for those skilled in the art that many variations and modifications can be done within the scope of the invention as described in the specification and defined with reference to the claims below. It may in particular be appreciated that a distal holder, which herein has been described as comprising two members, a holder member and a locking pin, can be in the form of a single member, which then is releasably engaged in a locking member, e.g. threaded or keyed into a locking member. Similarly, an actuation assembly, which herein also has been described as comprising two members, a retractor and a pusher, can be in the form of a single member, which then is releasably engaged in a proximal portion of a tubular member, e.g. threaded or keyed into a tubular member. It may also be pointed out that the insertion and delivery assembly or tool described herein could, with minor modifications, be used to operate a closure device that is of a unitary construction, i.e. with an integrated locking member. In fact, the locking member described above could be regarded as part of a holder to releasably engage the holder in a distal portion of a tubular member. An insertion assembly comprising a motor that effectuates a relative movement between two members could also be used in combination with other types of closure devices than the closure device described herein, and in particular in combination with a closure device that comprises an expandable distal portion and an expandable proximal portion, which are designed to be positioned on each side of a tissue wall. Other parts, in particular a locking pin and a holder member, of an insertion assembly could also be used in combination with other types of closure devices, and in particular closure devices comprising an expandable distal portion and an expandable proximal portion.

The invention claimed is:

1. A medical apparatus comprising:
   a closure device comprising:
      a first member or portion adapted to be placed on one side of an opening in a wall of a bodily organ, and
      a second member or portion adapted to be placed on the opposite side of the opening in the wall of the bodily organ,
   an insertion assembly comprising a first actuator operatively connected to one of said first and second members or portions, and a second actuator operatively connected to the other of the first and second members or portions,
   wherein the first actuator and the second actuator are separate and distinct from one another,
   wherein the insertion assembly has only one motor adapted to maneuver at least one of the first and second actuators.

2. A medical apparatus according to claim 1, wherein the closure device has a longitudinal central axis and comprises a tubular member having a length and an expandable distal portion extending between a distal end portion and a central portion and an expandable proximal portion extending between said central portion and a proximal end portion, and
   wherein the insertion assembly further comprises a distal holder, the holder being releasably engaged in the distal end portion and one of the first and second actuators being releasably engaged with the proximal end portion, and, in response to a relative movement between the holder and the one of the first and second actuators, the closure device is reversibly movable between a first elongated introduction configuration and a second positioning configuration in which either of the distal and proximal end portions have been moved towards each other such that said expandable distal and/or proximal portions have expanded radially away from said longitudinal central axis, wherein the one motor effectuates a relative movement between the holder and the one of the first and second actuators, and wherein said relative movement causes the closure device to move from the first elongated introduction configuration to the second positioning configuration.

3. A medical apparatus according to claim 2, wherein the insertion assembly further comprises a central holder, the central holder being releasably engaged in the central portion.

4. A medical apparatus according to claim 2, wherein the closure device further comprises a locking member, which has a distal end and a proximal end, and said distal and proximal ends comprise radial protrusions, and said distal end has at least one outer cross-sectional dimension larger than at least one inner cross-sectional dimension of the distal end portion and said proximal end has at least one outer cross-sectional dimension larger than at least one inner cross-sectional dimension of the proximal end portion, and the distance between the distal and proximal ends is smaller than a length of the tubular member.

5. A medical apparatus according to claim 4, wherein the closure device has a third closed configuration in which the locking member is positioned in the tubular member such that the distal end portion abuts the radial protrusions of the distal end and at least one enlarged inner cross-sectional dimension of the proximal end prevents further compression of the tubular member.

6. A medical apparatus according to claim 2, wherein the holder comprises a locking pin and a tubular holder member having a distal end provided with grip members, and the locking pin is adapted to be disposed inside the tubular holder member, to prevent the grip members from approaching each other.

7. A medical apparatus according to claim 2, wherein the first and second actuators comprises a pusher and a retractor, a distal end of which is upended, and wherein the proximal end portion of the tubular member is fixated between the upended distal end of the retractor and a distal end of the pusher.

8. A medical apparatus according to claim 7, wherein the retractor is slidably arranged inside the pusher, such that, when the pusher is moved closer to a distal end of the holder and the retractor abuts radial protrusions of the proximal end of a locking member, the pusher pushes the proximal end portion of the tubular member over radial protrusions of the proximal end of the locking member.

9. A medical apparatus according to claim 8, wherein the insertion assembly is provided with a safety mechanism to prevent a user from prematurely causing the pusher to push the proximal end portion of the tubular member over the radial protrusions of the proximal end of the locking member.

10. A medical apparatus according to claim 2, wherein the insertion assembly further comprises a delivery catheter, which is used to control the expansion of the distal and proximal expandable portions.

11. A medical apparatus according to claim 1, wherein the closure device is adapted for closing a septal defect in a heart.

12. A medical apparatus according to claim 1, wherein the closure device is adapted for closing a puncture in a vessel wall.

13. A medical apparatus according to claim 1, further comprising a suture which connects the first and second members or portions.

14. A medical apparatus according to claim 1, wherein the closure device has a longitudinal central axis and comprises a tubular member having a length and an expandable distal portion extending between a distal end portion and a central portion and an expandable proximal portion extending between said central portion and a proximal end portion,
wherein the first member or portion is one of the expandable distal portion and the expandable proximal portion and the second member or portion is the other of the expandable distal portion and the expandable proximal portion, such that the first actuator is operatively connected to one of the expandable distal portion and the expandable proximal portion and the second actuator is operatively connected to the other of the expandable distal portion and the expandable proximal portion.

15. A medical apparatus comprising:
a closure device comprising:
a first member or portion adapted to be placed on one side of an opening in a wall of a bodily organ, and
a second member or portion adapted to be placed on the opposite side of the opening in the wall of the bodily organ, and
an insertion assembly comprising a first motor and a second motor,
wherein the first motor is configured to actuate the first member or portion and the second motor is configured to actuate the second member or portion.

16. A medical apparatus according to claim 15, further comprising a suture which connects the first and second members or portions.

17. A medical apparatus according to claim 16, wherein the closure device has a longitudinal central axis and comprises a tubular member having a length and an expandable distal portion extending between a distal end portion and a central portion and an expandable proximal portion extending between said central portion and a proximal end portion,
wherein the first member or portion is one of the expandable distal portion and the expandable proximal portion and the second member or portion is the other of the expandable distal portion and the expandable proximal portion, such that the first motor is configured to actuate one of the expandable distal portion and the expandable proximal portion and the second motor is configured to actuate the other of the expandable distal portion and the expandable proximal portion.

* * * * *